(12) United States Patent
Lyon

(10) Patent No.: US 6,632,197 B2
(45) Date of Patent: *Oct. 14, 2003

(54) CLEAR VIEW CANNULA

(76) Inventor: Thomas R. Lyon, 3540 Wayne Ave., Apt. 11P, Bronx, NY (US) 10467

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/293,284

(22) Filed: Apr. 16, 1999

(65) Prior Publication Data

US 2001/0049493 A1 Dec. 6, 2001

(51) Int. Cl.[7] .................................. A61M 29/00
(52) U.S. Cl. .................... 604/107; 604/106; 604/264
(58) Field of Search ........................ 604/104–107, 604/164.01, 164.02, 164.04, 164.03, 164.06, 164.07, 164.09, 164.1, 164.11, 264, 174, 175, 523, 538, 533–536, 537; 600/141, 201, 204, 203, 215, 216, 235; 606/192, 198

(56) References Cited

U.S. PATENT DOCUMENTS

| | | | |
|---|---|---|---|
| 698,447 A | * 4/1902 | Bush | |
| 827,193 A | * 7/1906 | Thrash | |
| 872,217 A | * 11/1907 | Bonesteel | |
| 1,155,169 A | * 9/1915 | Starkweather | |
| 2,482,622 A | 9/1949 | Kahn | |
| 2,556,783 A | * 6/1951 | Wallace | 128/321 |
| 3,108,595 A | * 10/1963 | Overment | 128/350 |
| 3,241,554 A | * 3/1966 | Coanda | 128/350 |
| 3,261,357 A | * 7/1966 | Roberts et al. | 128/348 |
| 3,397,699 A | * 8/1968 | Kohl | 128/349 |
| 3,821,956 A | 7/1974 | Gordhamer | |
| 4,608,965 A | * 9/1986 | Anspach, Jr. et al. | 128/4 |
| 4,699,611 A | 10/1987 | Bowden | |
| 4,995,868 A | * 2/1991 | Brazier | 604/105 |
| 5,002,557 A | 3/1991 | Hasson | |
| 5,009,643 A | 4/1991 | Reich et al. | |
| 5,171,223 A | * 12/1992 | Herzberg | 604/104 |
| 5,197,971 A | * 3/1993 | Bonutti | 606/192 |
| 5,217,451 A | 6/1993 | Freitas | |
| 5,279,575 A | 1/1994 | Sugarbaker | |
| 5,295,994 A | * 3/1994 | Bonutti | 606/192 |
| 5,325,848 A | * 7/1994 | Adams et al. | 600/206 |
| 5,423,763 A | 6/1995 | Helland et al. | |
| 5,484,442 A | 1/1996 | Melker et al. | |
| 5,556,411 A | 9/1996 | Taoda et al. | |
| 5,591,191 A | 1/1997 | Kieturakis | |
| RE35,459 E | 2/1997 | Jonkman | |
| 5,632,761 A | 5/1997 | Smith et al. | |
| 5,637,097 A | 6/1997 | Yoon | |
| 5,749,883 A | * 5/1998 | Halpern | 606/159 |
| 5,885,258 A | * 3/1999 | Sachdeva et al. | 604/281 |
| 5,928,260 A | * 7/1999 | Chin et al. | 606/200 |
| 5,957,900 A | * 9/1999 | Ouchi | 604/264 |

* cited by examiner

*Primary Examiner*—Brian L. Casler
*Assistant Examiner*—Cris Rodriguez
(74) *Attorney, Agent, or Firm*—Stephen E. Feldman, P.C.

(57) ABSTRACT

There is disclosed a clear view cannula for use in surgical procedures having a tubular body, a cylindrical sleeve mounted about and slidably secured to the tubular body, and a plurality of shield members secured to the cylindrical sleeve. The cylindrical sleeve is slidably movable relative to the tubular body causing the shield members to expand and deploy such that the shield members retain torn and fragmented soft tissue within an anatomical cavity. Means are provided on the tubular body to co-act with means on the cylindrical sleeve to lock the expanded and deployed shield members and secure the tubular body within an anatomical body.

10 Claims, 3 Drawing Sheets

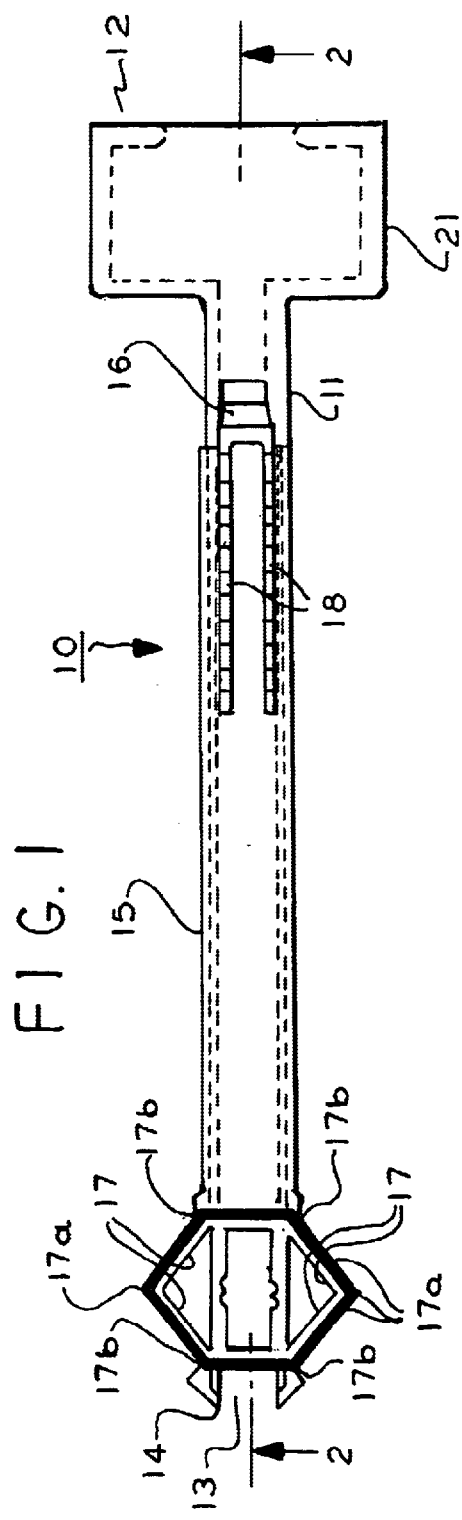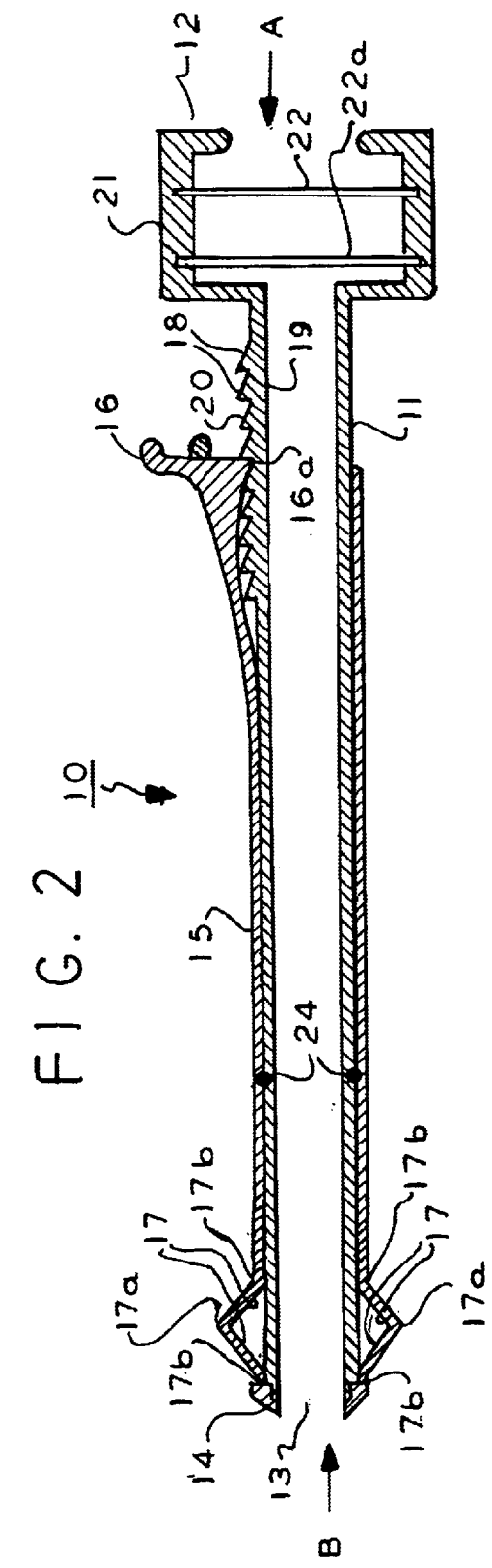

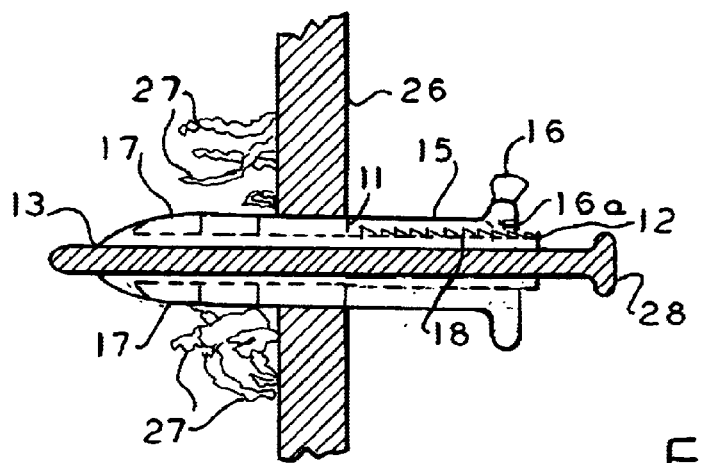
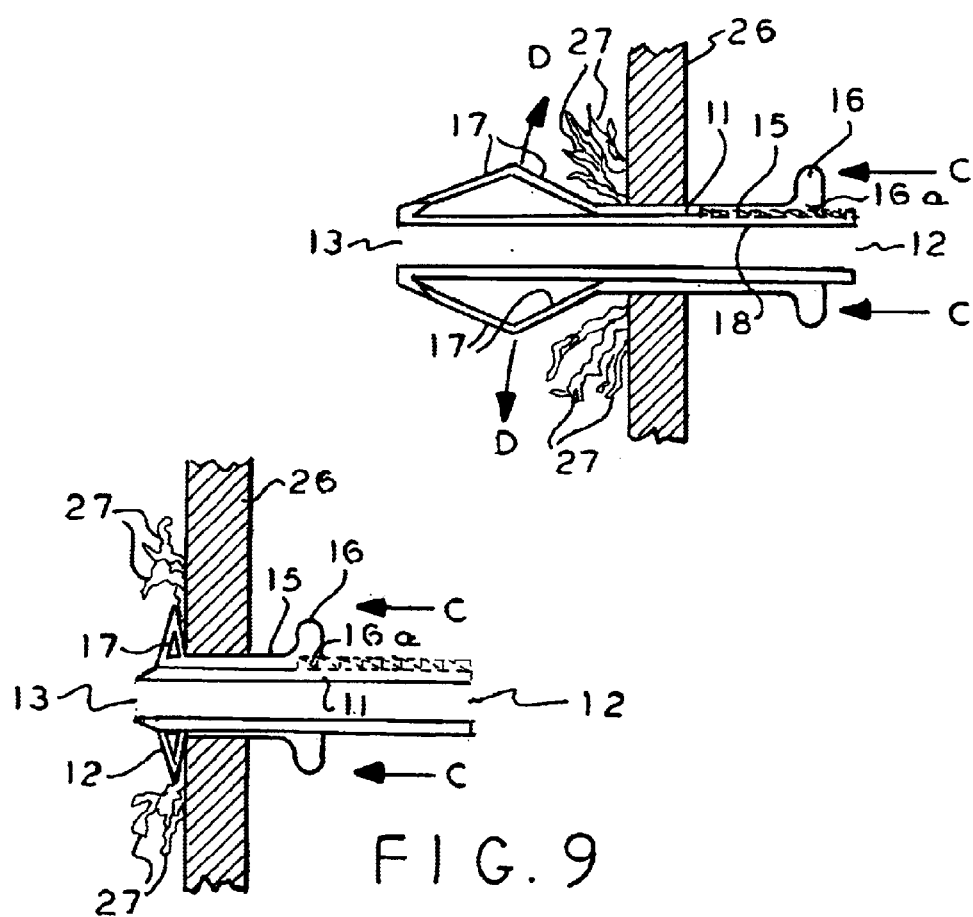

CLEAR VIEW CANNULA

FIELD OF THE INVENTION

This invention relates to a clear view cannula for use in surgical procedures. More particularly, this invention relates to a clear view cannula that permits an operator to insert the cannula through a body wall into an anatomical cavity, maintain the cannula in its inserted position, and introduce an auxiliary surgical instrument into the anatomical cavity through the cannula without visual or mechanical obstruction within the body wall.

BACKGROUND OF THE INVENTION

The use of surgical instruments such as cannulas to introduce an auxiliary surgical instrument into a body such as a joint, abdominal cavity, or the like is well known and widely used. A typical procedure can include making a small incision in the desired portion of the body wall, inserting a cannula into and through the incision and introducing an auxiliary surgical instrument through the cannula into the body to perform a further procedure.

In order to be thoroughly effective and minimize trauma to a patient, it is desirable in such procedures that the cannula be capable of being anchored or secured and not slip out of the anatomical cavity thereby preventing its reinsertion and that fragmented or torn soft tissue not have to be removed from the area surrounding the insertion point of the cannula in order to ensure that the auxiliary instrument can be used without visual or mechanical obstruction.

Several attempts have been proposed to overcome these problems and deficiencies. For example, U.S. Pat. No. 5,217,451 to Freitas discloses a trocar assembly having first and second cylindrical members secured to one another at the distal end of the assembly and a sleeve portion having a series of radially extending flexible members. This device has many small parts and is operable through the use of an interacting gear mechanism. Since the radially extending members, when fully deployed, form an acute angle substantially less than 90 degrees with respect to the longitudinal axis of the cylindrical members, they are not capable of effectively retaining or retracting torn or fragmented soft tissue within a body cavity; that is, the spaces between the fully deployed members permit torn or fragmented soft tissue to visually and mechanically obstruct the use of an instrument such as a camera that is typically introduced through a cannula prior to performing a surgical procedure.

U.S. Pat. No. 5,632,761 to Smith, et.al. discloses a device used to dissect and retract layers of tissue while a portion of the device is retained in a patient. The device utilizes two balloons, the first of which is inserted between layers of tissue and inflated to dissect the tissue layers after which the balloon is deflated. The second balloon is then positioned between the tissue layers and inflated to retract the tissue layers. The device includes a tube coaxially mounted to a delivery portion. The tube has a contracting portion and is provided with a number of deformable, longitudinally extending segments. This device also has many small moving parts and, due to the spherical shape of the second balloon, is not capable of fully retracting torn or fragmented soft tissue. Consequently, the device would have to be inserted deeper into a patient in order to be fully effective.

U.S. Pat. No. 5,637,097 to Yoon discloses an instrument used to penetrate an anatomical cavity having a fixed or retractable penetrating member, the distal end of which is used for penetration, and a portal sleeve having an expandable portion fixed relative to the penetrating member. This instrument, as with the devices described above, comprises many components and functions primarily to anchor the instrument within an anatomical cavity. The anchoring component is not designed to effectively retract or retain torn or fragmented soft tissue within the anatomical cavity.

These illustrative devices typically comprise many parts requiring costly and time consuming assembly. Since they are of relatively complex construction, subsequent cleaning and sterilization would also be costly and time consuming. In addition, these devices are not designed to effectively retract and retain torn or fragmented tissue within an anatomical cavity while, at the same time, anchoring the device within the cavity so that only a minimal portion of the device is retained in the cavity. Due to their complex structures, these devices are cumbersome to handle and manipulate by an operator. Furthermore, these illustrative devices are typically designed to function within a relatively large body cavity such as the abdomen where maneuverability is relatively unrestricted.

SUMMARY OF THE INVENTION

It has now been found that the shortcomings of such prior art devices are overcome by the clear view cannula of this invention. In general, the clear view cannula of the invention comprises: a tubular body having a proximate end and a distal end; a plurality of closely spaced teeth members formed on the outer surface and extending parallel to the longitudinal axis of said tubular body intermediate its proximate and distal ends; a cylindrical sleeve having a proximate end and a distal end concentrically mounted about and slidably secured to said tubular body; means at the proximate end of said cylindrical sleeve to engage said teeth members; and, a plurality of spaced apart shield members circumferentially disposed about and longitudinally co-extensive with said tubular body secured to the distal end of said cylindrical sleeve such that when said cylindrical sleeve is slidably urged along said tubular body toward the distal end of said tubular body, said shield members are caused to expand and deploy enabling said shield members to retract and retain torn or fragmented soft tissue within an anatomical cavity and anchor said clear view cannula within an anatomical cavity with a minimum of penetration of said clear view cannula into an anatomical cavity.

The means to secure the cylindrical sleeve to the teeth members as the cylindrical sleeve is slidably moved along the tubular body is readily provided by a detent depending from a raised shoulder at the proximate end of the cylindrical sleeve.

The shield members at the distal end of the cylindrical sleeve and are manufactured so as to be capable of being flexed intermediate their ends enabling them to be fully deployed and expanded within an anatomical cavity.

In one embodiment, the shield members are provided with an expandable web member so that when the shield members are fully deployed, the expandable web member fills the spaces between them thereby further assuring that any torn or fragmented tissue is completely retracted and retained within the body of a cavity.

Although the clear view cannula of the invention can readily be used in large body cavities such as the abdomen, it is particularly useful in smaller cavities such as joints; i.e., knees, shoulders, elbows, ankles, and the like. During arthroscopic surgery of a joint, the joint is typically inflated with water as opposed to a gas which is typically used in abdominal surgical procedures as the surgical procedures performed within a joint are significantly different from those performed within an abdominal cavity.

For example, the inside of a joint such as the knee is lined with a layer of a friable tissue called the synovium which is about ½ cm. thick. In patients about to undergo arthroscopic surgery, the synovial tissue is often inflamed and is also frequently torn and fragmented. In addition, there is present in the anterior portion of the knee joint a patella fat pad (or blob of fat tissue) which generally measures about 3×5 cm. square. Thus, inflamed and/or torn and fragmented synovial tissue and the patella fat pad in the knee joint serve to restrict and impede visualization of the joint cavity by the surgeon. However, this restricted vision is completely overcome when using the clear view cannula of the invention.

BRIEF DESCRIPTION OF THE DRAWING

The clear view cannula of the invention will become more apparent from the ensuing description when considered together with the accompanying drawing wherein:

FIG. 1 is a plan view of one embodiment of the clear view cannula of the invention, part shown in phantom to illustrate further details thereof;

FIG. 2 is an elevation sectional view of the clear view cannula shown in FIG. 1 taken substantially on the line 2—2 of FIG. 1;

FIG. 7 is a schematic side sectional view illustrating insertion of the clear view cannula of FIG. 1 through a body wall and into an anatomical cavity;

FIG. 8 is a schematic, partly fragmented side sectional view illustrating partial expansion and deployment of the shield members of the clear view cannula shown in FIG. 7; and, FIG. 9 is a schematic, partly fragmented side sectional view illustrating the shield members shown in FIG. 8 in a fully expanded and deployed position within an anatomical cavity.

DETAILED DESCRIPTION OF THE DRAWING AND THE INVENTION

Figure 3:
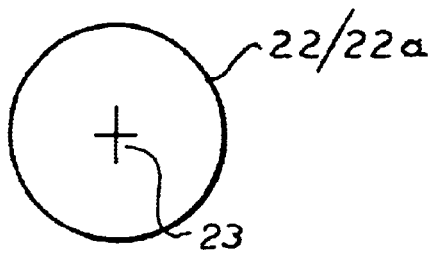
FIG. 3 is a view looking substantially in the direction of arrow A of FIG. 2.

Turning now to the drawing wherein like reference numerals and letters identify like parts, there is shown in FIGS. 1 and 2 one embodiment of the clear view cannula of the invention generally identified by reference numeral 10 which typically comprises a tubular cannula body 11 having a proximate end 12 and a distal end 13 which is normally tapered as indicated at 14 to facilitate entry or penetration of the cannula 10 through a body wall and into an anatomical cavity.

A cylindrical sleeve 15 is concentrically mounted about and slidably secured to the cannula body 11 in a close fitting relationship. The cylindrical sleeve 15 extends from adjacent the proximate end 12 of cannula body 11 toward the distal end 13 of cannula body 11 a distance of from about ½ to about ¾ the length of the cannula body 11. Cylindrical sleeve 15 is provided with a raised shoulder 16 at its proximate end and a plurality of spaced apart shield members 17 secured to its distal end. The shield members 17, shown partially deployed in FIGS. 1 and 2, are circumferentially disposed about and longitudinally co-extensive with the cannula body 11. Cylindrical sleeve 15 can be secured to the cannula body 11 by any suitable and conventional means such as apertures formed in the cannula body 11 which mate with nipples on the inner surface of the cylindrical sleeve 15 in a snap-fit relationship (not shown). Other means such as spot welding, fusion, and the like, can also be readily used as will be apparent to those skilled in this art.

As can be best seen in FIG. 2, a plurality of closely spaced apart teeth members 18 are provided on the outer, circumferential wall of the cannula body 11 and extend from the proximate end 12 toward the distal end 13 a distance of from about ½ to about ¾ of the length of the cannula body 11; that is, teeth members 18 are provided along the cannula body 11 for a distance about equal to the length of cylindrical sleeve 15. Teeth members 18 are formed to have a substantially perpendicular face 19 and a rear portion 20 that slopes toward proximate end 12. Preferably, the sloping rear portion 20 of each tooth member 18 terminates at the base of the perpendicular face 19 of each preceding tooth member 18. The inner end of shoulder 16 is formed to terminate in a depending detent 16a which engages the faces 19 of the teeth members 18 as described more fully hereinbelow.

The proximate end 12 of cannula body 11 is provided with a handle 21 which can be in any geometrical form that will enable a user to readily grasp the handle 21 with the fingers one hand and concurrently manipulate the cylindrical sleeve 15 toward and away from the distal end 13 of the cannula body 11 with another finger of the same hand. For example, the geometric form of handle 21 can be oblong, spherical, round, square or rectangular as such forms will readily enable a user to comfortably and easily grasp the handle 21 and manipulate the cylindrical sleeve 15 with the fingers of one hand while retaining complete control of the cannula 10.

A pair valve members 22 and 22a (FIG. 2) are secured within handle 21 to prevent liquid within a joint or body cavity from leaking out of the proximate end 12 of the cannula 10 after the cannula 10 has been inserted into a body cavity. Valve members 22 and 22a can be provided from any suitable flexible material such as rubber or latex that will prevent seepage or leakage of fluid from a body cavity through the proximate end 12 of the cannula 10. A crossshaped or X-shaped slit 23 is formed in each of the valve members 22 and 22a to enable an instrument to be inserted through the valve members 22 and 22a and through the cannula body 11.

To further prevent leakage or seepage of fluid from a body cavity, a gasket such as a rubber or latex O-ring 24 is seated between the outer circumferential surface of cannula body 11 and the inner circumferential surface of cylindrical sleeve 15 intermediate the proximate end 12 and the distal end 13 of cannula 10 as shown in FIG. 2.

As illustrated in FIGS. 1 and 2, shield members 17 are formed to have a cross-sectional thickness at their approximate mid-points indicated by 17a that is thinner than the cross-sectional thickness at their extremities indicated by 17b. This enables shield members 17 to be readily flexed from a substantially flat, at rest condition to a fully deployed condition after the cannula 10 has been inserted into a body cavity.

Figure 4:
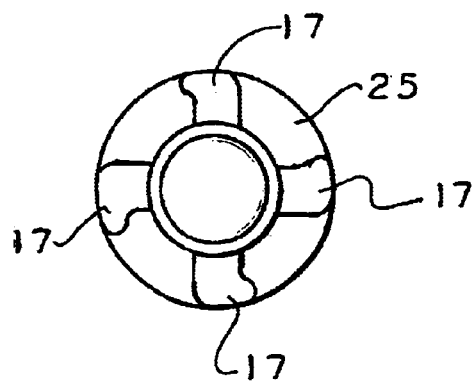
FIG. 4 is a view looking substantially in the direction of arrow B of FIG. 2.

FIG. 4 illustrates the configuration of the shield members 17 when fully deployed within a body cavity. In order to fill the spaces between the shield members 17, an expandable web member 25 can be secured to the shield members 17 to further assure that any torn or fragmented tissue is completely retracted and retained within a body cavity when the shield members 17 are fully deployed.

FIGS. 7, 8 and 9 of the drawing illustrate typical, sequential steps that can be employed in using the clear view cannula of the invention. As can be seen in FIG. 7, the cannula body 11, is shown being inserted through a body wall 26 and into an anatomical cavity such as a knee joint. Although insertion is typically made through a pre-formed incision, such insertion and penetration generally results in torn and fragmented soft tissue 27 which can obstruct or otherwise interfere with the use of an auxiliary surgical instrument. Such obstruction or interference is virtually eliminated by using the clear view cannula of the invention.

FIG. 7 also shows the insertion of a trocar 28 through cannula body 11 which is typically initially introduced into a body cavity and then subsequently removed and replaced with a surgical instrument such as a camera.

After the cannula body 11 has been inserted through the body wall 26 as shown in FIG. 7, an operator, using only finger tip pressure against shoulder 16, simply urges cylindrical sleeve 15 to slide along the cannula body 11 in the direction of arrows C as illustrated in FIG. 8. This causes shield members 17 to expand and deploy in the direction of arrows D toward the fragmented and torn tissue 27. As an operator continues to expand and deploy the shield members 17 in this manner, the operator can also withdraw the cannula body 11 outwardly through the body wall 26. Accidently fully withdrawing the cannula body 11 through the body wall 26 is prevented by the partially expanded and deployed shield members 17 contacting and engaging the inner surface of the body wall 26. As the operator withdraws the cannula body 11 outwardly, the shield members 17 are maintained in their partially expanded and deployed condition by annular detent 16a firmly and securely engaging the perpendicular face 19 of a tooth member 18. Urging of the cylindrical sleeve 15 to slide along the cannula body 11 is facilitated by the sloping rear portions 20 of the teeth members 18.

Typically, an operator will continue to slidably urge the cylindrical sleeve 15 along the annular body 11 and withdraw the cannula body 11 through the body wall 26 in this manner until the shield members 17 are fully expanded and deployed retaining the torn and fragmented tissue 27 against the inner surface of the body wall 26 with only a small portion of the distal end 13 of the cannula body 11 retained and locked in place within the body wall 26 as illustrated in FIG. 9. At this time, the shield members 17 are locked in their fully expanded and deployed condition and the cannula body 11 is firmly secured within the body wall 26 by means of the detent 16a engaging the perpendicular face 19 of a tooth member 18.

Figure 5:
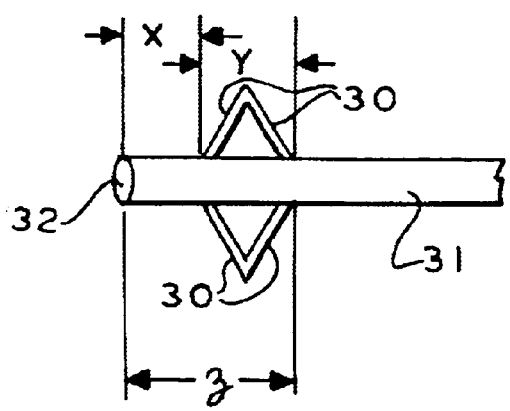
FIG. 5 is a schematic, partly fragmented side elevational view of a prior art cannula showing deployment of flexible members at its distal end.

In FIG. 5 there is illustrated a typical prior art cannula such as that disclosed in U.S. Pat. No. 5,217,451 to Freitas discussed above. As can be seen in FIG. 5, when the flexible members 30 of this prior art cannula are fully deployed, they form an acute angle of substantially less than 90 degrees with respect to the longitudinal axis of a cannula body 31. Consequently, torn and fragmented tissue can not be effectively retained within an anatomical cavity which would, in turn, interfere with an operator's view within the cavity.

Since the flexible members 30 (FIG. 5) when fully deployed form an acute angle, they encompass a distance "y" along the cannula body 31. This prevents the cannula body 31 from being withdrawn from within a body cavity which, in turn, creates a further distance "x" from the distal end 32 of the cannula body 31. Consequently, the distal end 32 of this cannula body 31 will extend into a body cavity the distance indicated by "z"; i.e., the sum of distances "y" and "x".

Figure 6:
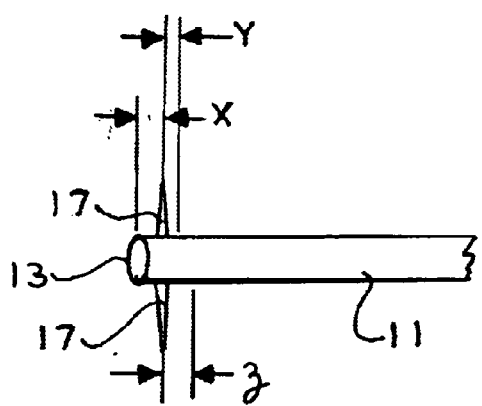
FIG. 6 is a schematic, partly fragmented side elevational view of the cannula of the invention showing deployment of the shield members at its distal end.

By contrast, the structure and operation of the clear view cannula of the invention permits its shield members 17 to be deployed at an angle that is substantially coincidental to 90 degrees with respect to the longitudinal axis of the cannula body as is illustrated in FIG. 6. This results in substantially reducing both the "x" and "y" distances enabling the cannula body 11 to be withdrawn through the wall of a body cavity until its withdrawal is arrested by the deployed shield members 17 and optionally, the expandable web member 25, leaving only a relatively small portion of its distal end 13 extending into a body cavity as is shown in FIG. 6. Thus, the total distance "z" that the cannula body 11 of the present invention extends into a body cavity is significantly and substantially less than the prior art cannula illustrated in FIG. 5. This significant and substantial reduction of extension into a body cavity is highly advantageous, particularly when surgical procedures are to be performed within the very limited confines of a body joint.

The materials used to fabricate the clear view cannula of the invention are not critical provided they are suitable for use in surgical procedures. For ease of fabrication, assembly and use, all components of the clear view cannula of the invention; i.e., the cannula body 11 carrying teeth members 18, cylindrical sleeve with annular collar 16 and detent 16a, and shield members 17 are preferably fabricated from well known and commercially available plastic materials that are suitable for use in surgical procedures.

Although the clear view cannula of the invention has been described in detail and with particularity, it will be appreciated by those skilled in this art that changes and modifications can be made therein without departing from the scope and spirit of the invention.

What is claimed is:

1. A clear view cannula adapted for use by a single hand of a surgeon and configured for an arthroscopic penetration through a body wall of a patient, the clear view cannula comprising:

a cannula including a tubular body having a distal end and a proximal end portion, the tubular body defining a through hole aligned with the longitudinal axis, the tubular body including a plurality of teeth members on the outer surface and extending parallel to the longitudinal axis of the tubular body, the distal end having a tapered tip adapted for making an arthroscopic portal through a body wall of a patient, a single piece handle positioned on the proximal end portion of the tubular body, the handle being adapted for readily grasping by a single hand of a surgeon; and a cylindrical sleeve having a distal end portion and a proximal end portion, the cylindrical sleeve being concentrically mounted about and slidably secured for translation relative to the tubular body, a distal edge of the distal end portion of the cylindrical sleeve being connected to the distal end of the tubular body, the cylindrical sleeve and tubular body defining a first position of the cannula, the first position being adapted for insertion through the body wall of the patient, the proximal end portion of the sleeve including a shoulder, the shoulder having a depending detent configured for selectively engaging the plurality of teeth and limiting the movement of the cylindrical sleeve relative to the tubular body, the shoulder being adapted for manipulation by the fingers of the single hand of the surgeon such that the relative positions of the tubular body and cylindrical sleeve of the cannula can be controlled by the single hand of the surgeon while gripping the handle, and the distal end portion including a plurality of shield members connected to the distal end of the tubular body, the plurality of shield members being configured for moving between the first position of the cannula parallel with the longitudinal axis and a second position of the cannula substantially perpendicular to the longitudinal axis, the cannula being adapted for manipulation by a single hand of a surgeon for the movement between the first and the second positions, the shield members being configured for bending about the mid-points upon the application of distally directed pressure upon the shoulder relative to the tubular body, the shield members in the second position being configured to improve the internal visibility through the arthroscopic portal by retracting and retaining the torn or fragmented tissue associated with the arthroscopic portal against the inner surface of the body wall.

2. The clear view cannula of claim 1, wherein the cylindrical sleeve has four shield members, the shield members having a first cross-sectional thickness at their mid-points less than a second cross-sectional thickness at the extremities.

3. The clear view cannula of claim 2, wherein the shield members are configured to retain the clear view cannula in position within the arthroscopic portal.

4. The clear view cannula of claim 1, wherein the distal end of the tubular body is tapered to facilitate penetration of the tubular body into the body wall of the patient and into an anatomical cavity.

5. The clear view cannula of claim 1, wherein the shield members are positioned from the first position to the second position by a finger tip pressure by the single hand against the shoulder of the cylindrical sleeve in a distal direction relative to the tubular body.

6. A clear view cannula adapted for use by a single hand of a surgeon and adapted for minimizing the depth of an arthroscopic penetration through a body wall of a patient, the clear view cannula comprising:

a cannula including a tubular body having a distal end and a proximal end portion, the tubular body defining a through hole aligned with the longitudinal axis, the tubular body including a plurality of teeth members on the outer surface and extending parallel to the longitudinal axis of the tubular body, the distal end having a tapered tip adapted for making an arthroscopic portal through a body wall of a patient, a single piece handle positioned on the proximal end portion of the tubular body, the handle being adapted for readily grasping by a single hand of a surgeon; and a cylindrical sleeve having a distal end portion and a proximal end portion, the cylindrical sleeve being concentrically mounted about and slidably secured for translation relative to the tubular body, a distal edge of the distal end portion of the cylindrical sleeve being connected to the distal end of the tubular body, the cylindrical sleeve and tubular body defining a first position of the cannula, the first position being adapted for insertion through the body wall of the patient, the proximal end portion of the sleeve including a shoulder, the shoulder having a depending detent configured for selectively engaging the plurality of teeth and limiting the movement of the cylindrical sleeve relative to the tubular body, the shoulder being adapted for manipulation by the fingers of the single hand of the surgeon such that the relative positions of the tubular body and cylindrical sleeve of the cannula can be controlled by the single hand of the surgeon while gripping the handle, and the distal end portion including a plurality of shield members connected to the distal end of the tubular body, the plurality of shield members being configured for moving between the first position of the cannula parallel with the longitudinal axis and a second position of the cannula substantially perpendicular to the longitudinal axis, the tapered tip being configured to extend a minimal finite distance distally beyond the plurality of shield members, the cannula in the second position being adapted to extend a minimal finite distance into the patient defined by the tapered tip and the shield members in the expanded position, the cannula being adapted for manipulation by a single hand of a surgeon for the movement between the first and the second positions, the shield members being configured for bending about the mid-points upon the application of distally directed pressure upon the shoulder relative to the tubular body.

7. The clear view cannula of claim 6, wherein the cylindrical sleeve has four shield members, the shield members having a first cross-sectional thickness at their mid-points less than a second cross-sectional thickness at the extremities.

8. The clear view cannula of claim 6, wherein the shield members are configured to retain the clear view cannula in position within the arthroscopic portal and configured to improve the internal visibility through the arthroscopic portal by retracting and retaining the torn or fragmented tissue associated with the arthroscopic portal against the inner surface of the body wall.

9. The clear view cannula of claim 6, wherein the distal end of the tubular body is tapered to facilitate penetration of the tubular body into the body wall of the patient and into an anatomical cavity.

10. The clear view cannula of claim 6, wherein the shield members are positioned between the first position to the second position by a finger tip pressure by the single hand against the shoulder of the cylindrical sleeve in a distal direction relative to the tubular body.

* * * * *